United States Patent [19]
Gande et al.

[11] Patent Number: 5,877,344
[45] Date of Patent: Mar. 2, 1999

[54] POLYMERIZATION INHIBITION OF ACRYLATES USING BLENDS OF NITROXIDES

[75] Inventors: Matthew E. Gande, Danbury; Glen T. Cunkle, Stamford, both of Conn.; Leslie R. Gatechair, Katonah, N.Y.; Stephen D. Pastor, Danbury, Conn.; Raymond Seltzer, New City; Roland A.E. Winter, Armonk, both of N.Y.

[73] Assignee: Ciba Specialty Chemicals Corporation, Tarrytown, N.Y.

[21] Appl. No.: 876,017

[22] Filed: Jun. 13, 1997

[51] Int. Cl.$^6$ .................................................. C07C 69/52
[52] U.S. Cl. ............................................... 560/205
[58] Field of Search .............................................. 560/205

[56] References Cited

U.S. PATENT DOCUMENTS 5,171,888 12/1992 Roling .
5,221,461 6/1993 Henrici et al. .
5,221,764 6/1993 Roling .
5,504,243 4/1996 Sakamoto et al. .

FOREIGN PATENT DOCUMENTS 0522709 1/1993 European Pat. Off. .

*Primary Examiner*—Paul J. Killos
*Attorney, Agent, or Firm*—Luther A. R. Hall

[57] ABSTRACT

Ethylenically unsaturated carboxyl monomers, such as acrylic or methacrylic acid or their esters, are protected from premature polymerization during manufacture and storage in the presence or absence of water by the incorporation therein of an effective stabilizing amount of a blend two or more nitroxides. Some of these blends provide synergistic stabilization efficacy much superior to the stabilization results obtained by use of either nitroxide alone.

42 Claims, No Drawings

POLYMERIZATION INHIBITION OF ACRYLATES USING BLENDS OF NITROXIDES

The present invention relates to a composition and to a process for reducing premature polymerization of readily polymerizable unsaturated monomers containing carboxy, ester or nitrile functionality during monomer manufacturing processes by incorporating therein an effective stabilizing amount of a mixture of two or more nitroxide compounds.

BACKGROUND OF THE INVENTION

It is well known that ethylenically unsaturated monomers like vinyl aromatic compounds, such as styrene, α-methylstyrene, vinyltoluene or divinylbenzene or acrylic monomers, such as acrylonitrile, methacrylonitrile, acrylic acid, methacrylic acid and their esters and amides, or unsaturated esters such as vinyl acetate or unsaturated polyesters have a strong tendency to polymerize when subjected to elevated temperatures. Manufacturing processes for such monomers typically include distillations or handling at elevated temperatures.

Known inhibitors of acrylic monomer polymerization include phenothiazine, hydroquinone monomethyl ether, methylene blue and nitroxides. Phenothiazine, while unable to totally inhibit polymerization of acrylic monomers, is a commonly used co-additive. Recent patents claim phenylenediamines with soluble transition metal salts (U.S. Pat. No. 5,221,764), and aryl N-nitroso compounds (EP 0 522 709 A2) are active in acrylic monomer stabilization. U.S. Patent No. 5,504,243 teaches a ternary mixture of a soluble transition metal salt, nitroso compound and nitroxide are also effective as monomer inhibitors. However, there still remains a need for a compound to improve the stability of acrylic monomers during their processing. The need exists for a stable polymerization inhibitor system which will effectively and safely prevent the premature polymerization of unsaturated acrylate monomers during distillation and other purification processes, particularly if air is absent, and during organic-aqueous phase separations.

As indicated above, it is known that acrylonitrile, acrylic acid, methacrylic acid and their respective esters, which are generically referred to in this application as acrylates, have a tendency to undergo unwanted and premature polymerization at elevated temperatures. The industrial production of acrylates also yields several byproducts from which the desired monomer must be separated. One stage of this purification usually involves the partition of the acrylate between an organic and an aqueous phase. During this purification and subsequent steps, the acrylate can undergo a thermally induced polymerization. This undesired reaction must be limited and hopefully entirely repressed to insure that the reactors, tanks, pipes, etc. used to make, store and transport the monomer remain free or essentially free of high molecular weight polymeric material.

The production of acylic acid usually involves the catalytic gas-phase oxidation of propylene. During the purification processing of the monomer, the reaction stream often undergoes a partition between an organic and an aqueous phase. During this partition, a particular polymerization inhibitor may not partition sufficiently well into each of the two phases where it is needed to prevent the monomer from undergoing premature and unwanted polymerization. The instant invention pertains to the use of a mixture of two or more nitroxides which when used together provide synergistic stabilization efficacy to the acylate monomer during its preparation and purification, especially when it undergoes partition between an organic medium and water or even in a solely organic system.

OBJECTS OF THE INVENTION

One object of this invention is to provide a composition protected from premature polymerization. Another object is to provide a process for inhibiting the premature polymerization of ethylenically unsaturated acrylate monomers during the distillation purification steps by incorporating therein an effective amount of a synergistic mixture of two or more nitroxides.

DETAILED DESCRIPTION

The instant invention pertains to a composition for inhibiting the premature polymerization of an ethylenically unsaturated acrylate monomer which comprises (a) an ethylenically unsaturated acrylate monomer or mixture of monomers, and (b) an effective inhibiting amount of a synergistic mixture of two nitroxide compounds.

The unsaturated acrylate monomers include acrylic acid, methacrylic acid, the esters of acrylic and methacrylic acids, and acrylonitrile.

While a wide range of mixtures of nitroxides provide synergistic results, particularly effective are the 1:1 blends of 1-oxyl-2,2,6,6-tetramethylpiperidin-4-ol and either bis(1-oxyl-2,2,6,6-tetramethylpiperidin-4-yl) sebacate or 1-oxyl-2,2,6,6-tetra-methylpiperidin-4-yl butyrate; or the 1:1 blend of 1-oxyl-2,2,6,6-tetramethyl-4-acetamido-piperidine and 1-oxyl-2,2,6,6-tetramethylpiperidin-4-yl butyrate.

The synergistic stabilization afforded by the mixture of nitroxides is most pronounced when water is present during the purification steps, but synergism is also seen in solely organic systems as well.

While nitroxide compounds as a general class are effective polymerization inhibitors for a wide variety of monomers including the acrylates, the synergistic increase in stabilization efficacy can be demonstrated by use of a mixture of bis(1-oxyl-2,2,6,6-tetramethylpiperidin-4-yl) sebacate and 1-oxyl-2,2,6,6-tetramethylpiperidin-4-ol. While a wide variety of ratios afford synergistic inhibition, a 1:1 mixture appears very effective. Synergism is seen where the weight ratio of the two nitroxides is 10:1 to 1:10; preferably 3:1 to 1:3; and most preferably where the weight ratio of the two nitroxides is between 2:1 and 1:2.

The total concentration of the instant mixture of nitroxides is 1–10,000 ppm; preferably 1–2000 ppm; and most preferably 1 to 1000 ppm, based on the weight of monomer being stabilized.

Mixture of nitroxides useful in this invention are preferably selected from the group consisting of
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-(2-methoxyethoxy)piperidine,
1-oxyl-2,2,6,6-tetramethyl-4-(2-methoxyethoxyacetoxy) piperidine;
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate, 1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
1-oxyl-2,2,6,6-tetramethyl-4-allyloxy-piperidine;
1-oxyl-2,2,6,6-tetramethyl-4-acetamidopiperidine;
1-oxyl-2,2,6,6-tetramethyl-4-(N-butylformamido) piperidine;
N,N'-bis(1-oxyl-2,2,6,6-tetramethylpiperidin-4-yl) adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one),
1-oxyl-2,2,6,6-tetramethyl-4-(2,3-dihydroxypropoxy) piperidine,
1-oxyl-2,2,6,6-tetramethyl-4-(2-hydroxy-4-oxapentoxy) piperidine, and
di-tert-butyl nitroxyl.

The instant invention also pertains to a process of preventing the premature polymerization of an acrylate monomer by incorporating therein an effective synergistic stabilizing amount of a mixture of two nitroxide compounds.

The polymerization inhibitor compositions can be introduced into the monomer to be protected by any conventional method. It may be added as a concentrate solution in suitable solvents just upstream of the point of desired application by any suitable means. In addition, these compounds may be injected separately into the extraction or distillation train along with the incoming feed, or through separate entry points providing efficient distribution of the inhibitor composition. Since the inhibitor is gradually depleted during operation, it is generally necessary to maintain the appropiate amount of the inhibitor in the extraction or distillation apparatus by adding inhibitor during the course of the extraction or distillation process. Such addition may be carried out either on a generally continuous basis or it may consist of intermittently charging inhibitor into the extraction or distillation system if the concentration of inhibitor is to be maintained above the minimum required level.

The polymerization inhibiting compositions of this invention are also well suited for protecting the reboiler sections of a distillation column.

The following examples are meant for illustrative purposes only and are not to be construed as limiting the instant invention in any manner whatsoever.

Several methods to determine the efficacy of potential monomer stabilizers have been reported. One method involves laboratory scale distillations (EP 522,709 A2). The drawback of this method is that it requires a large amount of monomer and requires a detailed interpretation of the results such as a visual ranking of polymer build-up at various places in the distillation system. This method does not allow for a rapid screening of monomer inhibitors.

U.S. Pat. Nos. 5,171,888 and 5,221,461 report a method which involves simply heating a sample of monomeric material with a test stabilizer at a fixed temperature, usually between 80° C. and 150° C. and determining the time to exotherm. A modification of this method is described in U.S. Pat. No. 5,504,243 which uses the fact that poly(acrylic acid) is insoluble in acrylic acid. Thus, the failure time in this test is defined as the time to the formation of a visually observable polymer precipitate in the system. This method gives quick and reproducible results when used with neat acrylic acid or when the acrylic acid is partitioned between toluene and water.

In the Examples three different test methods are employed to determine the effectiveness of the nitroxide mixtures. The method is chosen to simulate different aspects of the purification processes.

METHOD 1

Acrylic acid is distilled to remove any storage stabilizer present. Stock stabilizer solutions (1.5 mg/mL) are prepared in propionic acid. This stock solution is added to the distilled acrylic acid to give a test solution having 5 ppm of total stabilizer. Aliquots of this test solution are then placed into three separate reaction tubes. Each tube is purged with a gas mixture (0.65% oxygen in nitrogen) for ten minutes. The tubes are then sealed and placed in a 110° C. oil bath. The tubes are watched till the appearance of visible polymer formation is observed as a precipitate. Failure times are reported as an average of at least three tubes as seen in Table 1.

METHOD 2

Test solutions are prepared as in Method 1. Aliquots (1 mL) of the test solution are placed into three separate reaction tubes. To each tube is added 0.5 mL of toluene and 0.5 mL of distilled water. Each tube is purged as described in Method 1 and then sealed. The tubes are placed in a 90° C. oil bath and heated till visible polymer is observed as a precipitate. Failure times are reported as an average of at least three tubes as seen in Tables 2 and 3.

METHOD 3

Method 3 is identical to Method 2 except that the test solution contains 2.5 ppm of total stabilizer. Failure times are reported as an average of at least three tubes as seen in Table 4.

TABLE 1

Stabilization of Neat Acrylic Acid (Method 1)

| Mixture of Components* (% by weight) | | Failure Time |
|---|---|---|
| A | B | (minutes) |
| none | none | 5 |
| 100 | 0 | 220 |
| 75 | 25 | 240 |
| 67 | 33 | 330 |
| 50 | 50 | 275 |
| 33 | 67 | 330 |
| 25 | 75 | 295 |
| 0 | 100 | 210 |

*A is bis(1-oxyl-2,2,6,6-tetramethylpiperidin-4-yl)sebacate.
B is 1-oxyl-2,2,6,6-tetramethylpiperidin-4-ol.

TABLE 2

Stabilization of Aqueous Acrylic Acid
(Method 2)

| Mixture of Components* (% by weight) | | Failure Time |
|---|---|---|
| A | B | (minutes) |
| none | none | 30 |
| 100 | 0 | 380 |
| 75 | 25 | 385 |
| 67 | 33 | 570 |
| 50 | 50 | 760 |
| 33 | 67 | 720 |
| 25 | 75 | 710 |
| 0 | 100 | 600 |

*A is bis(1-oxyl-2,2,6,6-tetramethylpiperidin-4-yl)sebacate.
B is 1-oxyl-2,2,6,6-tetramethylpiperidin-4-ol.

TABLE 3

Stabilization of Aqueous Acrylic Acid
(Method 2)

| Mixture of Components* (% by weight) | | | | Failure Time |
|---|---|---|---|---|
| B | C | D | E | (minutes) |
| none | none | none | none | 30 |
| 100 | 0 | 0 | 0 | 600 |
| 0 | 100 | 0 | 0 | 530 |
| 50 | 50 | 0 | 0 | 590 |
| 0 | 0 | 100 | 0 | 800 |
| 50 | 0 | 50 | 0 | 950 |
| 0 | 0 | 0 | 100 | 660 |
| 50 | 0 | 0 | 50 | 755 |

*B is 1-oxyl-2,2,6,6-tetramethylpiperidin-4-ol.
C is 1-oxyl-2,2,6,6-tetramethyl-4-n-propoxypiperidine.
D is 1-oxyl-2,2,6,6-tetramethylpiperidin-4-yl butyrate.
E is 1-oxyl-2,2,6,6-tetramethyl-4-(2-methoxyethoxyacetoxy)piperidine.

TABLE 4

Stabilization of Aqueous Acrylic Acid
(Method 3)

| Mixture of Components* (% by weight) | | | | Failure Time |
|---|---|---|---|---|
| B | D | F | G | (minutes) |
| 100 | 0 | 0 | 0 | 375 |
| 0 | 0 | 100 | 0 | 475 |
| 50 | 0 | 50 | 0 | 555 |
| 0 | 0 | 0 | 100 | 355 |
| 50 | 0 | 0 | 50 | 630 |
| 0 | 100 | 0 | 0 | 335 |
| 0 | 50 | 50 | 0 | 590 |
| 0 | 50 | 0 | 50 | 405 |

*B is 1-oxyl-2,2,6,6-tetramethylpiperidin-4-ol.
D is 1-oxyl-2,2,6,6-tetramethylpiperidin-4-yl butyrate.
F is 1-oxyl-2,2,6,6-tetramethyl-4-(2-methoxyethoxy)piperidine.
G is 1-oxyl-2,2,6,6-tetramethyl-4-acetamidopiperidine.

What is claimed is:

1. A composition for inhibiting the premature polymerization of an ethylenically unsaturated acrylate monomer which comprises
   (a) an ethylenically unsaturated acrylate monomer or mixture of monomers, and
   (b) an effective inhibiting amount of a synergistic mixture of two nitroxide compounds.

2. A composition according to claim 1 wherein the unsaturated acrylate monomer is acrylic acid, methacrylic acid, an ester of acrylic acid or methacrylic acid, or acrylonitrile.

3. A composition according to claim 2 wherein the acrylate monomer is acrylic acid.

4. A composition according to claim 2 wherein the acrylate monomer is acrylonitrile.

5. A composition according to claim 1 which additionally contains water.

6. A composition according to claim 1 wherein the effective stabilizing amount of the mixture of two nitroxide compounds is 1 to 10,000 ppm, based on the weight of monomer being stabilized.

7. A composition according to claim 6 wherein the effective stabilizing amount of the mixture of two nitroxide compounds is 1 to 2000 ppm.

8. A composition according to claim 7 wherein the effective stabilizing amount of the mixture of two nitroxide compounds is 1 to 1000 ppm.

9. A composition according to claim 1 wherein the weight ratio of the two nitroxides is 10:1 to 1:10.

10. A composition according to claim 9 wherein the weight ratio of the two nitroxides is 3:1 to 1:3.

11. A composition according to claim 10 wherein the weight ratio of the two nitroxides is 2:1 to 1:2.

12. A composition according to claim 1 wherein the two nitroxides are selected from the group consisting of
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-(2-methoxyethoxy)piperidine,
1-oxyl-2,2,6,6-tetramethyl-4-(2-methoxyethoxyacetoxy)piperidine;
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
1-oxyl-2,2,6,6-tetramethyl-4-allyloxy-piperidine;
1-oxyl-2,2,6,6-tetramethyl-4-acetamidopiperidine;
1-oxyl-2,2,6,6-tetramethyl-4-(N-butylformamido)piperidine;
N,N'-bis(1-oxyl-2,2,6,6-tetramethylpiperidin-4-yl) adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one),
1-oxyl-2,2,6,6-tetramethyl-4-(2,3-dihydroxypropoxy)piperidine, 1-oxyl-2,2,6,6-tetramethyl-4-(2-hydroxy-4-oxapentoxy) piperidine, and
di-tert-butyl nitroxyl.

13. A composition according to claim 1 wherein the mixture of nitroxides is a 1:1 blend of 1-oxyl-2,2,6,6-tetramethylpiperidin-4-ol and either bis(1-oxyl-2,2,6,6-tetra-methylpiperidin-4-yl) sebacate or 1-oxyl-2,2,6,6-tetramethylpiperidin-4-yl butyrate; or the 1:1 blend of 1-oxyl-2,2,6,6-tetramethyl-4- acetamidopiperidine and 1-oxyl-2,2,6,6-tetra-methylpiperidin-4-yl butyrate.

14. A composition according to claim 5 wherein the effective stabilizing amount of the mixture of two nitroxide compounds is 1 to 10,000 ppm, based on the weight of monomer being stabilized.

15. A composition according to claim 14 wherein the effective stabilizaing amount of the mixture of two nitroxide compounds is 1 to 2000 ppm.

16. A composition according to claim 15 wherein the effective stabilizing amount of the mixture of two nitroxide compounds is 1 to 1000 ppm.

17. A composition according to claim 5 wherein the weight ratio of the two nitroxides is 10:1 to 1:10.

18. A composition according to claim 17 wherein the weight ratio of the two nitroxides is 3:1 to 1:3.

19. A composition according to claim 18 wherein the weight ratio of the two nitroxides is 2:1 to 1:2.

20. A composition according to claim 5 wherein the two nitroxides are selected from the group consisting of
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-(2-methoxyethoxy)piperidine,
1-oxyl-2,2,6,6-tetramethyl-4-(2-methoxyethoxyacetoxy) piperidine;
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
1-oxyl-2,2,6,6-tetramethyl-4-allyloxy-piperidine;
1-oxyl-2,2,6,6-tetramethyl-4-acetamidopiperidine;
1-oxyl-2,2,6,6-tetramethyl-4-(N-butylformamido) piperidine;
N,N'-bis(1-oxyl-2,2,6,6-tetramethylpiperidin-4-yl) adipamide,
N-(1-oxyl-2,2,6,6-tetramethylpiperidin-4-yl)-caprolactam,
N-( 1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one),
1-oxyl-2,2,6,6-tetramethyl-4-(2,3-dihydroxypropoxy) piperidine,
1-oxyl-2,2,6,6-tetramethyl-4-(2-hydroxy-4-oxapentoxy) piperidine, and
di-tert-butyl nitroxyl.

21. A composition according to claim 5 wherein the mixture of nitroxides is a 1:1 blend of 1-oxyl-2,2,6,6-tetramethylpiperidin-4-ol and either bis(1-oxyl-2,2,6,6-tetra-methylpiperidin-4-yl) sebacate or 1-oxyl-2,2,6,6-tetramethylpiperidin-4-yl butyrate; or the 1:1 blend of 1-oxyl-2,2,6,6-tetramethyl-4-acetamidopiperidine and 1-oxyl-2,2,6,6-tetra-methylpiperidin-4-yl butyrate.

22. A process for preventing the premature polymerization of an unsaturated acrylate monomer by incorporating therein an effective synergistic stabilizing amount of a mixture of two nitroxide compounds.

23. A process according to claim 22 wherein the unsaturated acrylate monomer is acrylic acid, methacrylic acid, an ester of acrylic acid or methacrylic acid, or acrylonitrile.

24. A process according to claim 23 wherein the acrylate monomer is acrylic acid.

25. A process according to claim 23 wherein the acrylate monomer is acrylonitrile.

26. A process according to claim 22 where additionally water is present.

27. A process according to claim 22 wherein the effective stabilizing amount of the mixture of two nitroxide compounds is 1 to 10,000 ppm, based on the weight of monomer being stabilized.

28. A process according to claim 27 wherein the effective stabilizing amount of the mixture of two nitroxide compounds is 1 to 2000 ppm.

29. A process according to claim 28 wherein the effective stabilizing amount of the mixture of two nitroxide compounds is 1 to 1000 ppm.

30. A process according to claim 22 wherein the weight ratio of the two nitroxides is 10:1 to 1:10.

31. A process according to claim 30 wherein the weight ratio of the two nitroxides is 3:1 to 1:3.

32. A process according to claim 31 wherein the weight ratio of the two nitroxides is 2:1 to 1:2.

33. A process according to claim 22 wherein the two nitroxides are selected from the group consisting of
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-(2-methoxyethoxy)piperidine,
1-oxyl-2,2,6,6-tetramethyl-4-(2-methoxyethoxyacetoxy) piperidine;
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate, bis(1-oxyl-2,2,6,6-tetramethylpiperidin-4-yl) hexahydroterephthalate,
1-oxyl-2,2,6,6-tetramethyl-4-allyloxy-piperidine;
1-oxyl-2,2,6,6-tetramethyl-4-acetamidopiperidine;
1-oxyl-2,2,6,6-tetramethyl-4-(N-butylformamido)piperidine;
N,N'-bis(1-oxyl-2,2,6,6-tetramethylpiperidin-4-yl) adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine,
4,4'-ethylenebis (1-oxyl-2,2,6,6-tetramethylpiperazin-3-one),
1-oxyl-2,2,6,6-tetramethyl-4-(2,3-dihydroxypropoxy) piperidine,
1-oxyl-2,2,6,6-tetramethyl-4-(2-hydroxy-4-oxapentoxy) piperidine, and
di-tert-butyl nitroxyl.

34. A process according to claim 22 wherein the mixture of nitroxides is a 1:1 blend of 1-oxyl-2,2,6,6-tetramethylpiperidin-4-ol and either bis(1-oxyl-2,2,6,6-tetramethyl-piperidin-4-yl) sebacate or 1-oxyl-2,2,6,6-tetramethylpiperidin-4-yl butyrate; or the 1:1 blend of 1-oxyl-2,2,6,6-tetramethyl-4-acetamidopiperidine and 1-oxyl-2,2,6,6-tetramethyl-piperidin-4-yl butyrate.

35. A process according to claim 26 wherein the effective stabilizing amount of the mixture of two nitroxide compounds is 1 to 10,000 ppm, based on the weight of monomer being stabilized.

36. A process according to claim 35 wherein the effective stabilizaing amount of the mixture of two nitroxide compounds is 1 to 2000 ppm.

37. A process according to claim 36 wherein the effective stabilizing amount of the mixture of two nitroxide compounds is 1 to 1000 ppm.

38. A process according to claim 26 wherein the weight ratio of the two nitroxides is 10:1 to 1:10.

39. A process according to claim 38 wherein the weight ratio of the two nitroxides is 3:1 to 1:3.

40. A process according to claim 39 wherein the weight ratio of the two nitroxides is 2:1 to 1:2.

41. A process according to claim 26 wherein the two nitroxides are selected from the group consisting of
1-oxyl-2,2,6,6-tetramethylpiperidine,
1-oxyl-2,2,6,6-tetramethylpiperidin-4-ol,
1-oxyl-2,2,6,6-tetramethylpiperidin-4-one,
1-oxyl-2,2,6,6-tetramethyl-4-n-propoxypiperidine,
1-oxyl-2,2,6,6-tetramethyl-4-(2-methoxyethoxy)piperidine,
1-oxyl-2,2,6,6-tetramethyl-4-(2-methoxyethoxyacetoxy) piperidine;
1-oxyl-2,2,6,6-tetramethylpiperidin-4-yl stearate,
1-oxyl-2,2,6,6-tetramethylpiperidin-4-yl acetate,
1-oxyl-2,2,6,6-tetramethylpiperidin-4-yl butyrate,
1-oxyl-2,2,6,6-tetramethylpiperidin-4-yl 2-ethylhexanoate,
1-oxyl-2,2,6,6-tetramethylpiperidin-4-yl octanoate,
1-oxyl-2,2,6,6-tetramethylpiperidin-4-yl laurate,
1-oxyl-2,2,6,6-tetramethylpiperidin-4-yl benzoate,
1-oxyl-2,2,6,6-tetramethylpiperidin-4-yl 4-tert-butylbenzoate,
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
1-oxyl-2,2,6,6-tetramethyl-4-allyloxy-piperidine;
1-oxyl-2,2,6,6-tetramethyl-4-acetamidopiperidine;
1-oxyl-2,2,6,6-tetramethyl-4-(N-butylformamido) piperidine;
N,N'-bis(1-oxyl-2,2,6,6-tetramethylpiperidin-4-yl) adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine,
4,4'-ethylenebis(1-oxyl-2,2,6,6-tetramethylpiperazin-3-one),
1-oxyl-2,2,6,6-tetramethyl-4-(2,3-dihydroxypropoxy) piperidine,
1-oxyl-2,2,6,6-tetramethyl-4-(2-hydroxy-4-oxapentoxy) piperidine, and
di-tert-butyl nitroxyl.

42. A process according to claim 26 wherein the mixture of nitroxides is a 1:1 blend of 1-oxyl-2,2,6,6-tetramethylpiperidin-4-ol and either bis(1-oxyl-2,2,6,6-tetramethyl-piperidin-4-yl) sebacate or 1-oxyl-2,2,6,6-tetramethylpiperidin-4-yl butyrate; or the 1:1 blend of 1-oxyl-2,2,6,6-tetramethyl-4-acetamidopiperidine and 1-oxyl-2,2,6,6-tetramethyl-piperidin-4-yl butyrate.

* * * * *